United States Patent [19]
Jang

[11] Patent Number: 6,039,756
[45] Date of Patent: Mar. 21, 2000

[54] INTRAVASCULAR STENT

[76] Inventor: G. David Jang, 30725 Eastburn La., Redlands, Calif. 92374

[21] Appl. No.: 08/949,865

[22] Filed: Oct. 14, 1997

Related U.S. Application Data

[60] Provisional application No. 60/017,484, Apr. 26, 1996.

[51] Int. Cl.⁷ ............................................. A61F 2/06
[52] U.S. Cl. ................................................. 623/1
[58] Field of Search .................................... 623/1, 11, 12

[56] References Cited

U.S. PATENT DOCUMENTS

| | | | |
|---|---|---|---|
| 5,449,373 | 9/1995 | Pinchasik et al. | 606/198 |
| 5,697,971 | 12/1997 | Fischell | 623/1 |
| 5,776,161 | 7/1998 | Globerman | 623/1 |

FOREIGN PATENT DOCUMENTS

| | | | |
|---|---|---|---|
| 0 587 197 A1 | 3/1994 | European Pat. Off. | A61F 2/04 |
| 0 679 372 A2 | 11/1995 | European Pat. Off. | A61B 19/00 |
| 0 709 067 A2 | 5/1996 | European Pat. Off. | A61F 2/06 |
| 43 03 181 A1 | 8/1994 | Germany | A61M 29/00 |
| 296 08 037 U1 | 8/1996 | Germany | A61M 29/00 |
| WO96/03092 | 2/1996 | WIPO | A61F 2/02 |
| WO96/26689 | 9/1996 | WIPO | A61F 2/06 |

*Primary Examiner*—Michael J. Milano
*Attorney, Agent, or Firm*—Wilson Sonsini Goodrich & Rosati

[57] ABSTRACT

A stent in a non-expanded state includes a plurality of a first column expansion strut pairs that form a first expansion column, a plurality of second column expansion strut pairs that form a second expansion column and a plurality of first serial connecting struts that form a first connecting strut column. The first connecting strut column couples the first expansion column to the second expansion column. At least a portion of the plurality of the first serial connecting struts have a first stair-step and a second stair-step. The first expansion column, second expansion column, and first connecting strut column form a plurality of geometric cells. At least a portion of the plurality of geometric cells are asymmetrical geometric cells.

9 Claims, 14 Drawing Sheets

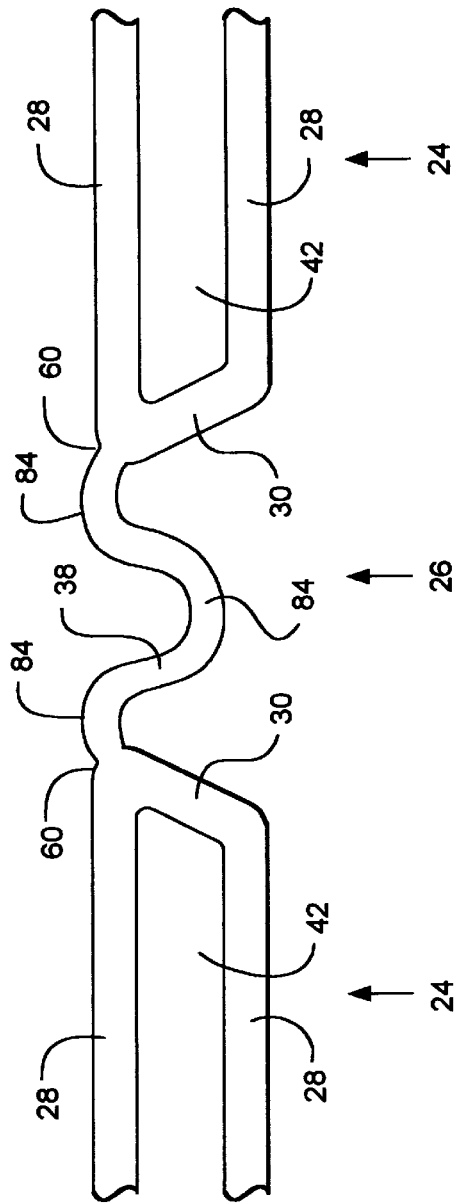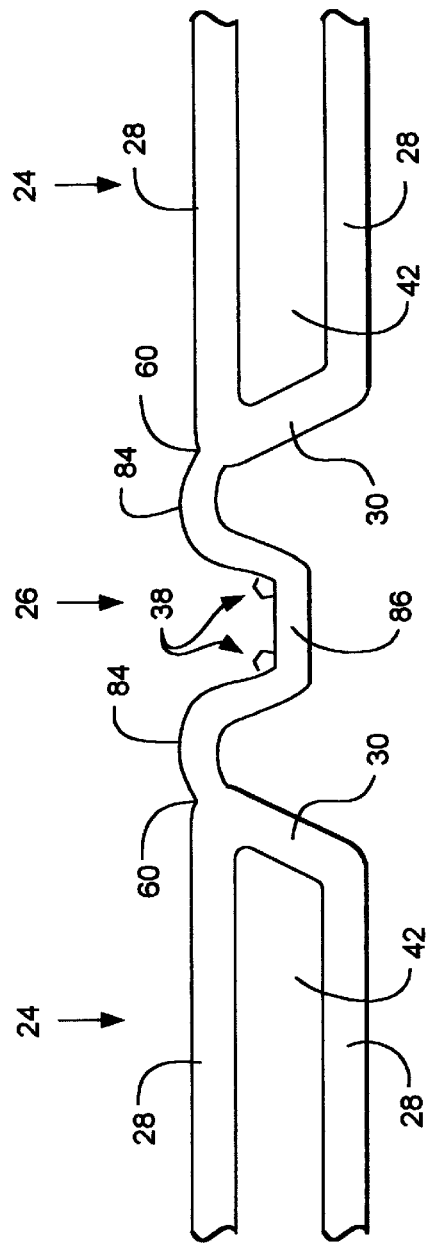

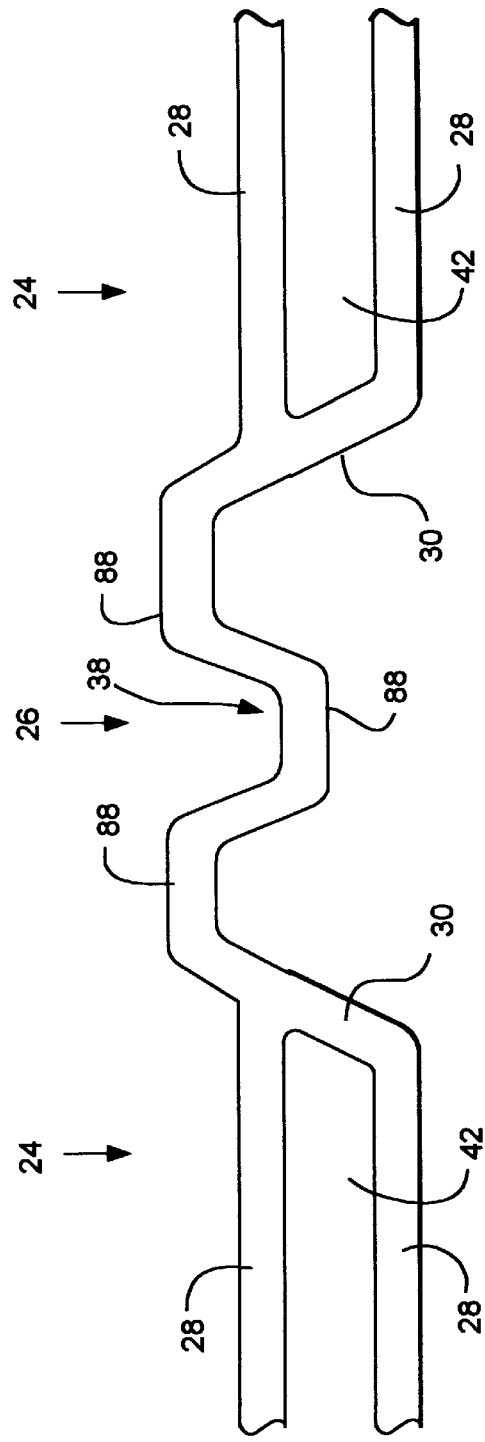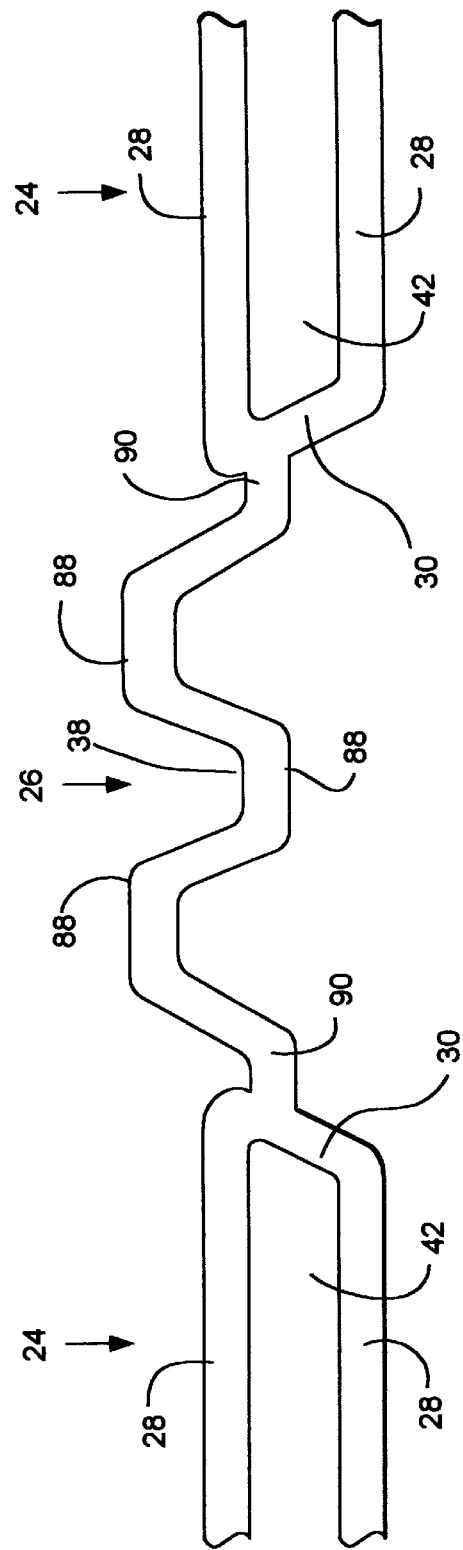

INTRAVASCULAR STENT

CROSS-REFERENCE TO RELATED APPLICATIONS

This application claims the benefit of Provisional Patent Application No. 60/017,484 filed Apr. 26, 1996, the disclosure of which is incorporated by reference. This application is related to U.S. patent application Ser. No. 08/824,142, filed Mar. 25, 1997, entitled "Intravascular Stent" and U.S. patent application Ser. No. 08/824,866, filed Mar. 26, 1997, entitled "Intravascular Stent", both having same named inventor G. David Jang and incorporated by reference.

BACKGROUND OF THE INVENTION

1. Field of the Invention

This invention relates to intravascular stents, and more particularly to an intravascular stent which provides easy introduction through tortious sections of vessels.

2. Description of the Related Art

Angioplasty, either coronary or general vascular, has advanced to become the most effective means for revascularization of stenosed vessels. In the early 1980's, angioplasty first became available for clinical practice in the coronary artery, and has since proven an effective alterative to conventional bypass graft surgery. Balloon catheter dependent angioplasty has consistently proven to be the most reliable and practical interventional procedure. Other ancillary technologies such as laser based treatment, or directional or rotational arthrectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational arthrectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for unstented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the multilink design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent, and no method of reinforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube.

Adjacent first meander patterns are connected by second meander patterns to form a generally uniform distributed pattern. The symmetrical arrangement with first and second meander patterns having sharp right angled bends allows for catching and snagging on the vessel wall during delivery. Furthermore, the large convolutions in the second meander pattern are not fully straightened out during expansion reducing rigidity and structural strength of the expanded stent. There is, further, no method of programming the stent diameter along its longitudinal axis to achieve a tapering stent design, and no method of reinforcement of stent ends or other regions is provided for.

These and other conventional stent designs suffer in varying degrees from a variety of drawbacks including: (a) inability to negotiate bends in vessels due to columnar rigidity of the unexpanded stent; (b) lack of structural strength, radial and axial lateral, of the unexpanded stent; (c) significant foreshortening of the stent during expansion; (d) limited stent length; (e) constant expanded stent diameter; (f) poor crimping characteristics; and (g) rough surface modulation of the unexpanded stent.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent which, (i) can be crimped tightly on the expansion balloon while maintaining a low profile and flexibility, (ii) has a smooth surface modulation when crimped over a delivery balloon, to prevent catching and snagging of the stent on the vessel wall during delivery or (iii) with reenforcement rings on the ends or middle or both to keep the ends of the stent securely positioned against the vessel walls of the target blood vessel.

SUMMARY OF THE INVENTION

Accordingly an object of the present invention is to provide a scaffold for an interior lumen of a vessel.

Another object of the invention is to provide a stent which prevents recoil of the vessel following angioplasty.

A further object of the invention is to provide a stent that maintains a larger vessel lumen compared to the results obtained only with balloon angioplasty.

Yet another object of the invention is to provide a stent that reduces foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduced tupeling of the vessel wall.

Another object of the invention is to provide a chain mesh stent that reduces vessel "hang up" in a tortious vessel or a vessel with curvature.

These and other objects of the invention are achieved in a stent in a non-expanded state. A plurality of a first column expansion strut pair form a first expansion column. A plurality of a second column expansion strut pair form a second expansion column. A plurality of first serial connecting struts form a first connecting strut column that couples the first expansion column to the second expansion column. At least a portion of the plurality of the first serial connecting struts have a first stair-step and a second stair-step. The first expansion column, second expansion column, and first connecting strut column form a plurality of geometric cells. At least a portion of the plurality of geometric cells are asymmetrical geometric cells.

In another embodiment, the stent in the non-expanded state includes a first expansion column formed of a plurality of first expansion struts, a second expansion column formed of a plurality of second expansion struts and a first connecting strut column formed of a plurality of first connecting struts. The first connecting strut column couples the first expansion column to the second expansion column. A first expansion strut in the first expansion column is circumferentially offset from a corresponding second expansion strut of the second expansion column. At least a portion of the plurality of first connecting struts include a first stair-step with a first slant angle and a second stair-step with a second slant angle.

In another embodiment, a stent assembly includes a balloon and an expandable stent positioned at an exterior of the balloon. The stent includes a first expansion strut. A plurality of the first expansion struts form a first expansion column. A plurality of second expansion struts form a second expansion column. A plurality of the first connecting struts form a first connecting strut column. Each of a first expansion strut of the first expansion column is coupled to a second expansion strut of the second expansion column. At least a portion of the plurality of first connecting struts include a first stair-step with a first slant angle and a second stair-step with a second slant angle.

BRIEF DESCRIPTION OF THE DRAWINGS

FIG. 7 is a drawing of another embodiment of a strut pattern of the stent of the present invention.

FIG. 8 is a drawing of another embodiment of a strut pattern of the stent of the present invention.

FIG. 9 is a drawing of another embodiment of a strut pattern of the stent of the present invention.

FIG. 10 is a drawing of another embodiment of a strut pattern of the stent of the present invention.

DETAILED DESCRIPTION

Figure 1A:
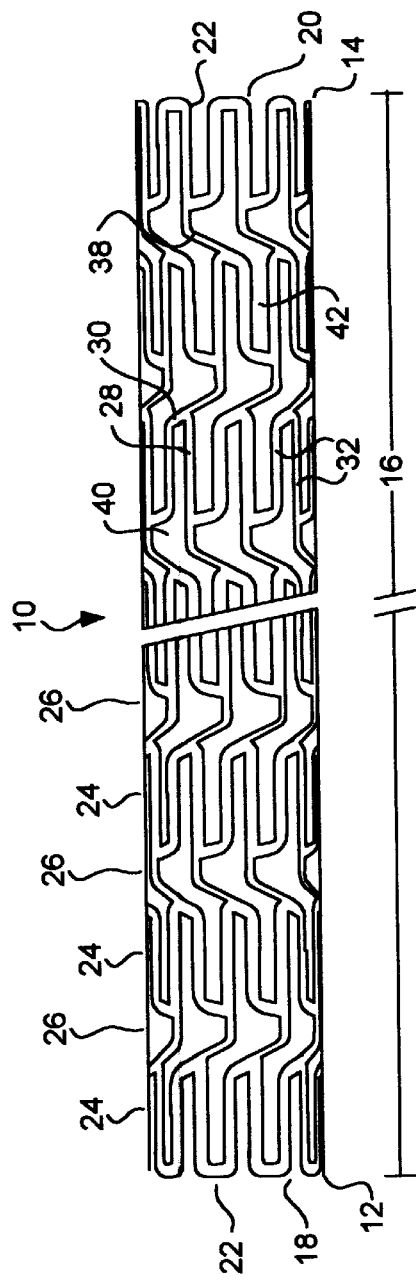
FIG. 1A is a side elevation view of the pre-expansion mode of an embodiment of the stent of the present invention.

A first embodiment of the present invention is shown in FIGS. 1A, 1B, 1C, 2A and 2B. Referring to FIG. 1A, an elongate hollow tubular stent 10 in an unexpanded state is shown. A proximal end 12 and a distal end 14 define a longitudinal length 16 of stent 10. The longitudinal length 16 of the stent 10 can be as long as 100 mm or longer. A proximal opening 18 and a distal opening 20 connect to an inner lumen 22 of stent 10. Stent 10 can be a single piece, without any seams or welding joints or may include multiple pieces.

Stent 10 is constructed of two to fifty or more expansion columns or rings 24 connected together by interspersed connecting strut columns 26. The first column on the proximal end 12 and the last column on the distal end 14 of stent 10 are expansion columns 24.

Expansion columns 24 are formed from a series of expansion struts 28, and joining struts 30. Expansion struts 28 are thin elongate members arranged so that they extend at least in part in the direction of the longitudinal axis of stent 10. When an outward external force is applied to stent 10 from the inside by an expansion balloon or other means, expansion struts 28 are reoriented such that they extend in a more circumferential direction, i.e along the surface of cylindrical stent 10 and perpendicular to its longitudinal axis. Reorientation of expansion struts 28 causes stent 10 to have an expanded circumference and diameter. In FIG. 1A, expansion struts 28 of unexpanded stent 10 are seen to extend substantially parallel to the longitudinal axis of stent 10.

Expansion struts 28 are joined together by joining struts 30 to form a plurality of expansion strut pairs 32. Expansion strut pairs have a closed end 34 and an open end 36. Additional joining struts 30 join together expansion struts 28 of adjacent expansion strut pairs 32, such that expansion struts 28 are joined alternately at their proximal and distal ends to adjacent expansion struts 28 to form expansion columns 24. Each expansion column 24 contains a plurality, typically eight to twenty, twenty to sixty, or larger of expansion struts 28.

Connecting struts 38 connect adjacent expansion columns 24 forming a series of interspersed connecting strut columns 26 each extending around the circumference of stent 10. Each connecting strut 38 joins a pair of expansion struts 28 in an expansion column 24 to an adjacent pair of expansion struts 28 in an adjacent expansion column 24. For stent 10 of FIG 1A, the ratio of expansion struts 28 in an expansion column 24 to connecting struts 38 in a connecting strut column 26 is two to one; however, this ratio in general can be x to 1 where x is greater or less than two. Furthermore, since the stent 10 of FIG. 1A begins with an expansion column 24 on the proximal end 12 and ends with an expansion column 24 on the distal end 14, if there are n expansion columns 24 with m expansion struts 28 per column, there will be m−1 connecting strut columns 26, and n(m−1)/2 connecting struts 38.

The reduced number of connecting struts 38 in each connecting strut column 26, as compared to expansion struts 28 in each expansion column 24, allows stent 10 to be longitudinally flexibility. Longitudinal flexibility can be further increased by using a narrow width connecting strut, providing additional flexibility and suppleness to the stent as it is navigated around turns in a natural blood vessel.

At least a portion of the open spaces between struts in stent 10 form asymmetrical cell spaces 40. A cell space is an empty region on the surface of stent 10, completed surrounded by one or a combination of stent struts, including expansion struts 28, connecting struts 38, or joining struts 30. Asymmetrical cell spaces 40 are cell spaces which have no geometrical symmetry i.e. no rotation, reflection, combination rotation and reflection or other symmetry.

Asymmetrical cell spaces 40 in FIG 1A are surrounded by a first expansion strut pair 32 in a first expansion column 24, a first connecting strut 38, a second expansion strut pair 32 in an adjacent expansion column 24, a first joining strut 30, a second connecting strut 38, and a second joining strut 30. Furthermore, expansion strut pairs 32 of asymmetrical cell space 40 may be circumferentially offset i.e. have longitudinal axes that are not collinear and have their open ends 36 facing each other. The space between two expansion struts of an expansion strut pair 32 is known as a loop slot 42.

Figure 1C:
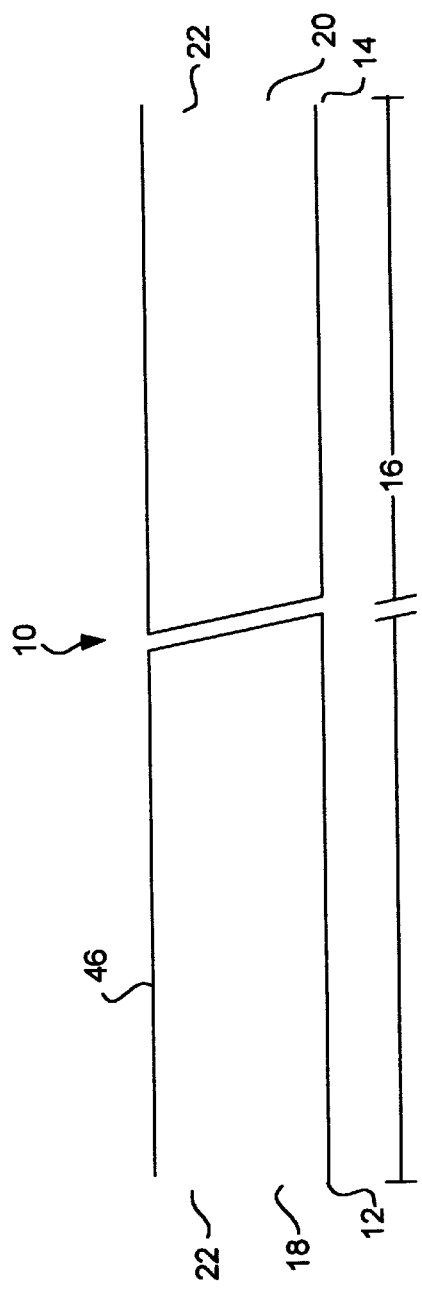
FIG. 1C is a longitudinal cross sectional view of an embodiment of the stent of the present invention.
Figure 1B:
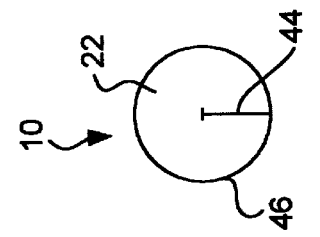
FIG. 1B is a cross sectional view of an embodiment of the stent of the present invention.

FIG. 1B shows inner lumen 22, radius 44 and stent wall 46 of stent 10. Stent wall 46 consists of stent struts including expansion struts 28, connecting struts 38 and joining struts 30.

FIG. 1C shows, proximal end 12, distal end 14, longitudinal length 16, inner lumen 22, and stent wall 46 of stent 10. Inner lumen 22 is surrounded by stent wall 46 which forms the cyllindrical surface of stent 10.

Figure 2A:
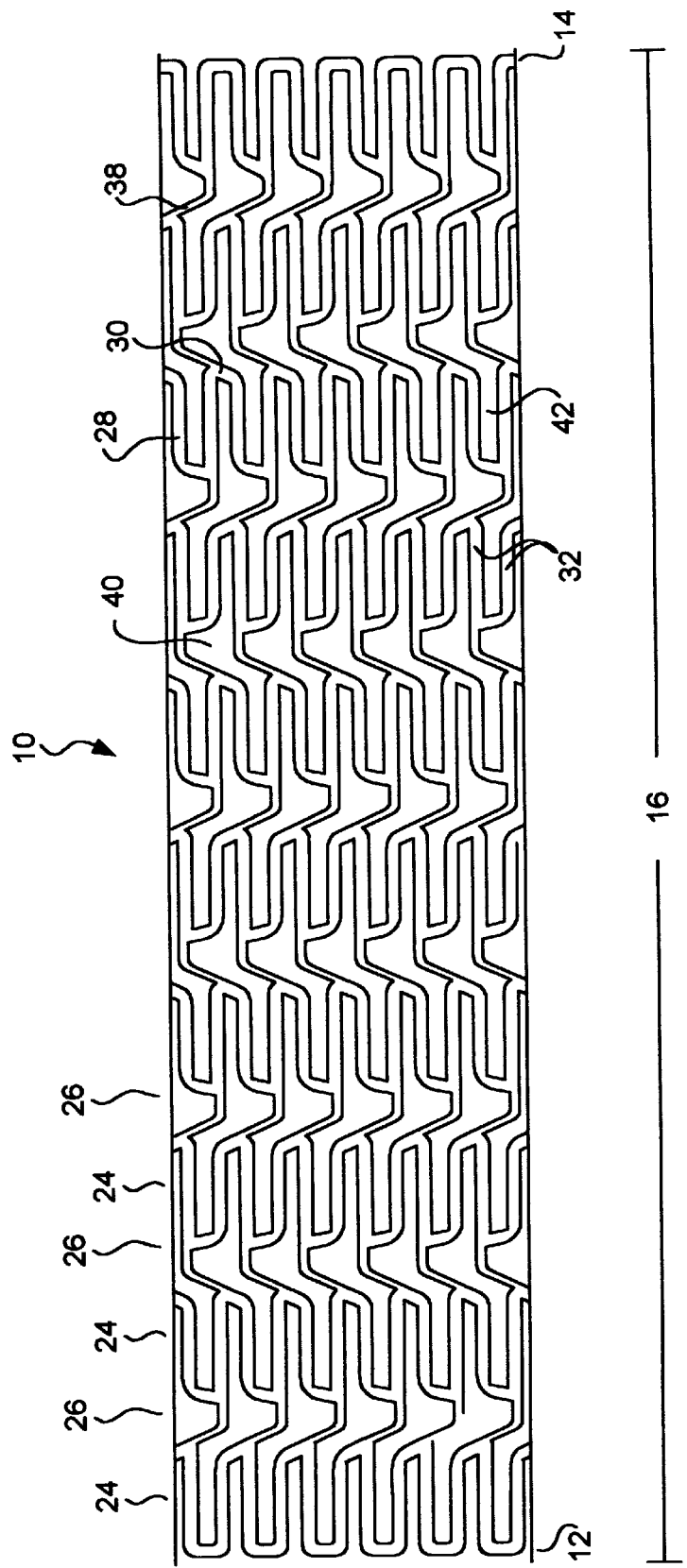
FIG. 2A is a drawing of the strut pattern of the stent of FIG. 1.
Figure 2B:
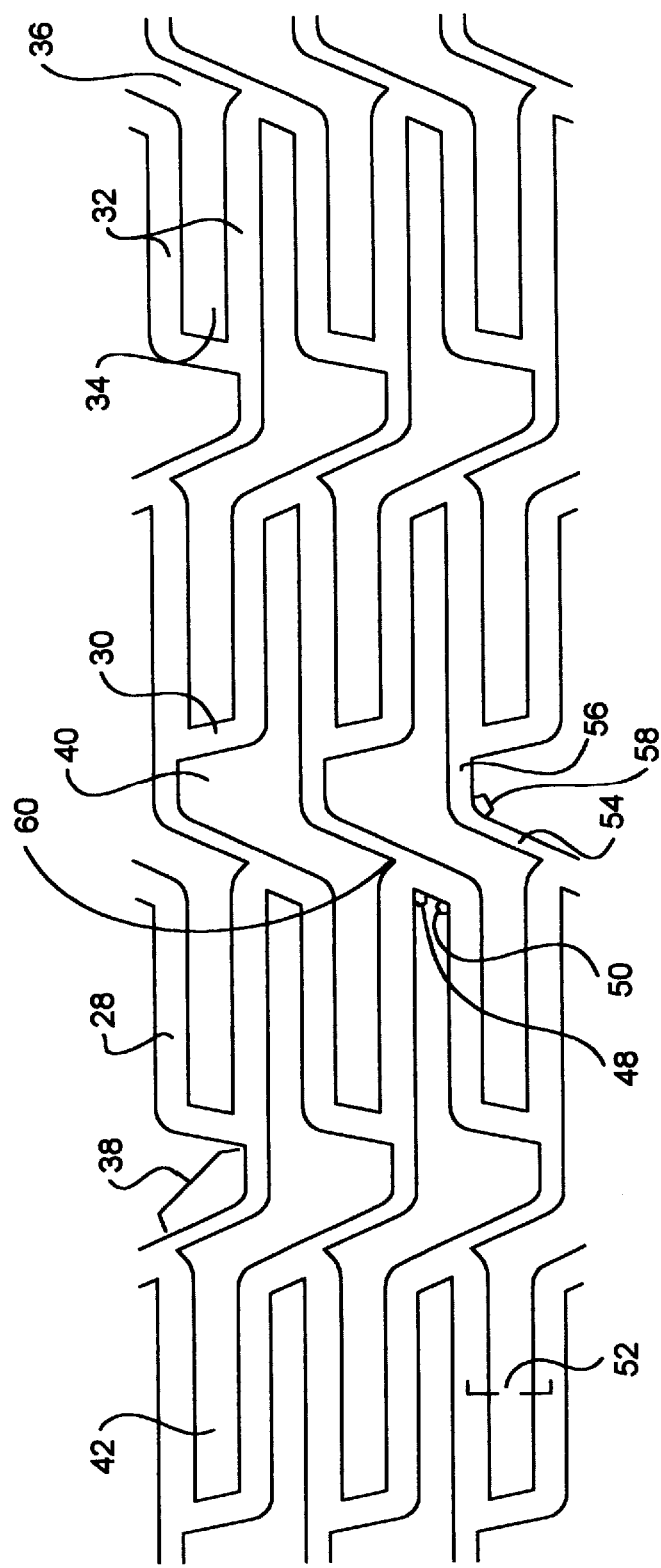
FIG. 2B is a close up view of the strut pattern of FIG. 2A.

Referring now to FIGS. 2A and 2B, joining struts 30 of stent 10 are seen to extend at an angle to the expansion struts 28, forming a narrow angle 48 with one expansion strut 28 in an expansion strut pair 32 and a wide angle 50 with the other expansion strut 28 of an expansion strut pair 32. Narrow angle 48 is less than ninety degrees, while wide angle 50 is greater than ninety degrees. Joining struts 30 extend both longitudinally along the longitudinal axis of stent 10 and circumferentially, along the surface of the stent 10 perpendicular its longitudinal axis.

Expansion strut spacing 52 between adjacent expansion struts 28 in a given expansion column 24 are uniform in stent 10 of FIGS. 2A and 2B; however, non-uniform spacings can also be used. Expansion strut spacings 52 can be varied, for example, spacings 52 between adjacent expansion struts 28 in an expansion column 24 can alternate between a narrow and a wide spacing. Additionally, spacings 52 in a single expansion column 24 can differ from other spacings 52 in other columns 24.

It is noted that varying expansion strut spacings 52 which form the loop slots 42 results in variable loop slot widths. Furthermore, the longitudinal axis of the loop slots 42 need not be collinear or even parallel with the longitudinal axis of loop slots 42 of an adjacent expansion column 24. FIGS. 2A and 2B show an arrangement of expansion struts 28 such that collinear, parallel adjacent loop slots 42 are formed, but non-collinear and non-parallel loop slots 42 can also be used.

Additionally the shape of loop slots 42 need not be the same among loop slots of a single or multiple expansion columns 24. The shape a loop slots 42 can be altered by changing the orientation or physical dimensions of the expansion struts 28 and/or joining struts 30 which connect expansion struts 28 of expansion strut pairs 32 defining the boundaries of loop slots 42.

Connecting struts 38 couple adjacent expansion columns 24, by connecting the distal end of an expansion strut pair in one expansion column 24 to the proximal end of an adjacent expansion strut pair 32 in a second expansion column 24. Connecting struts 38 of FIGS. 2A and 2B are formed from two linear sections, a first linear section 54 being joined at its distal end to a second linear section 56 at its proximal end to form a first slant angle 58.

The first linear section 54 of a connecting strut 38 is joined to expansion strut 28 at the point where joining strut 30 makes narrow angle 48 with expansion strut 28. First linear section 54 extends substantially collinear to joining strut 30 continuing the line of joining strut 30 into the space between expansion columns 24. The distal end of the first linear section 54 is joined to the proximal end of the second linear section 56 forming slant angle 58. Second linear section 56 extends substantially parallel to expansion struts 28 connecting at its distal end to joining strut 30 in an adjacent expansion column 24. The distal end of second linear section 56 attaches to expansion strut 28 at the point where joining strut 30 makes narrow angle 48 with expansion strut 28. Further, joining strut 30 can have a second slant angle with a width that can be the same or different from the width of the first slant angle.

FIGS. 2A and 2B show connecting struts 38 and joining struts 30 slanted relative to the longitudinal axis of stent 10, with the circumferential direction of the slanted struts alternating from column to adjacent column. Circumferential direction refers to the handedness with which the slanted struts wind about the surface of the stent 10. The circumferential direction of the slant of connecting strut first linear sections 54 in a connecting strut column 26 is opposite the circumferential direction of the slant of connecting strut first linear sections 54 in an adjacent connecting strut column 26. Similarly, the circumferential direction of the slant of joining struts 30 in an expansion column 24 is opposite the circumferential direction of the slant of joining struts 30 in an adjacent expansion column 24. Alternating circumferential slant directions of connecting struts 38 and joining struts 30 prevents axial warping of stent 10 during deliver and expansion. Other non-alternating slant direction patterns can also be used for connecting struts 38 or joining struts 30 or both.

One or more relief notches 60 can be formed where metal has been removed from a strut, usually at a joint where multiple struts are connected. Relief notches 60 increase flexibility of a strut or joint by creating a thinned, narrow region along the strut or joint. The positioning of a relief notch 60 gives added flexibility to the unexpanded stent.

Figure 3A:
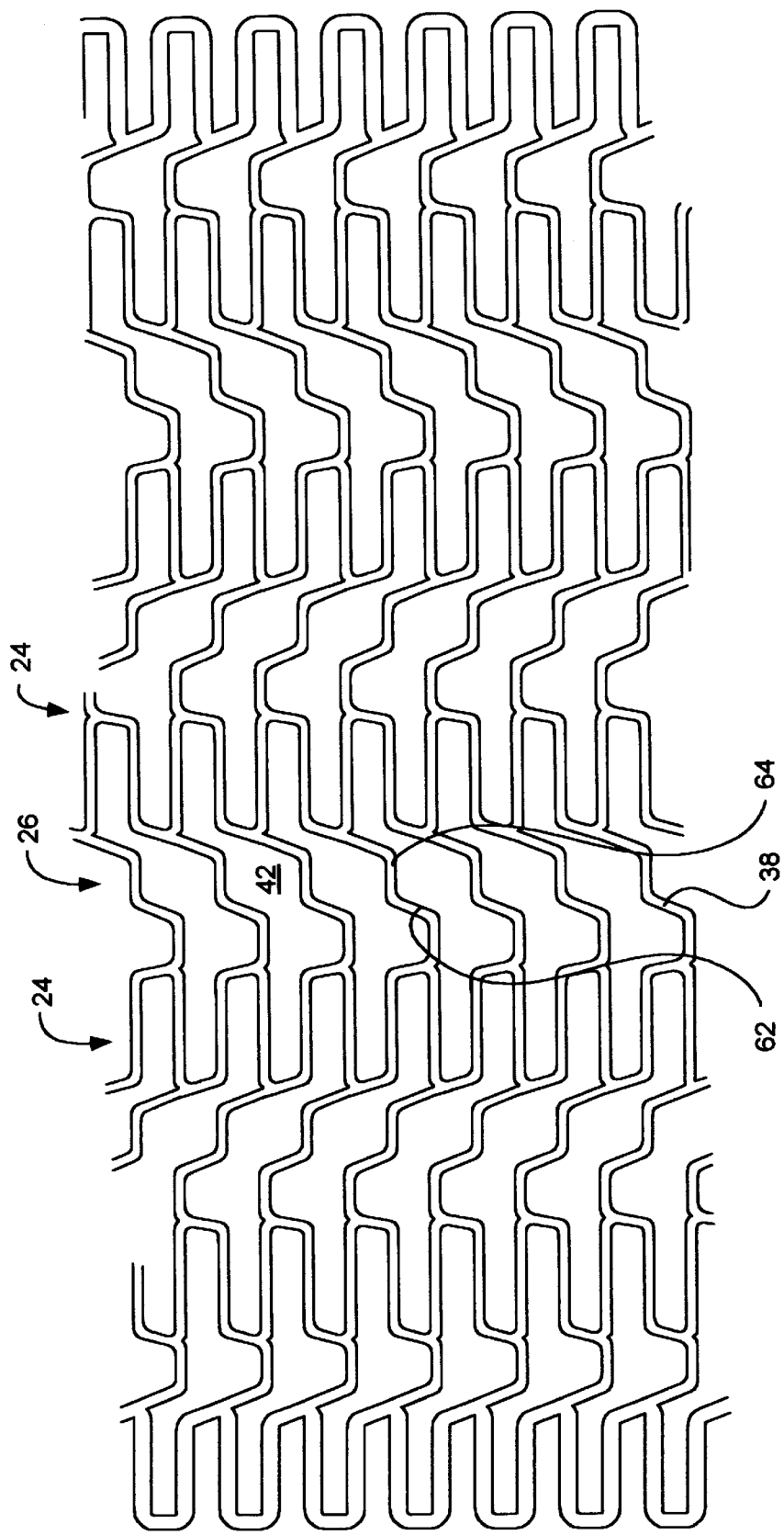
FIG. 3A is a drawing of a strut pattern of one embodiment of the stent of the present invention.
Figure 3B:
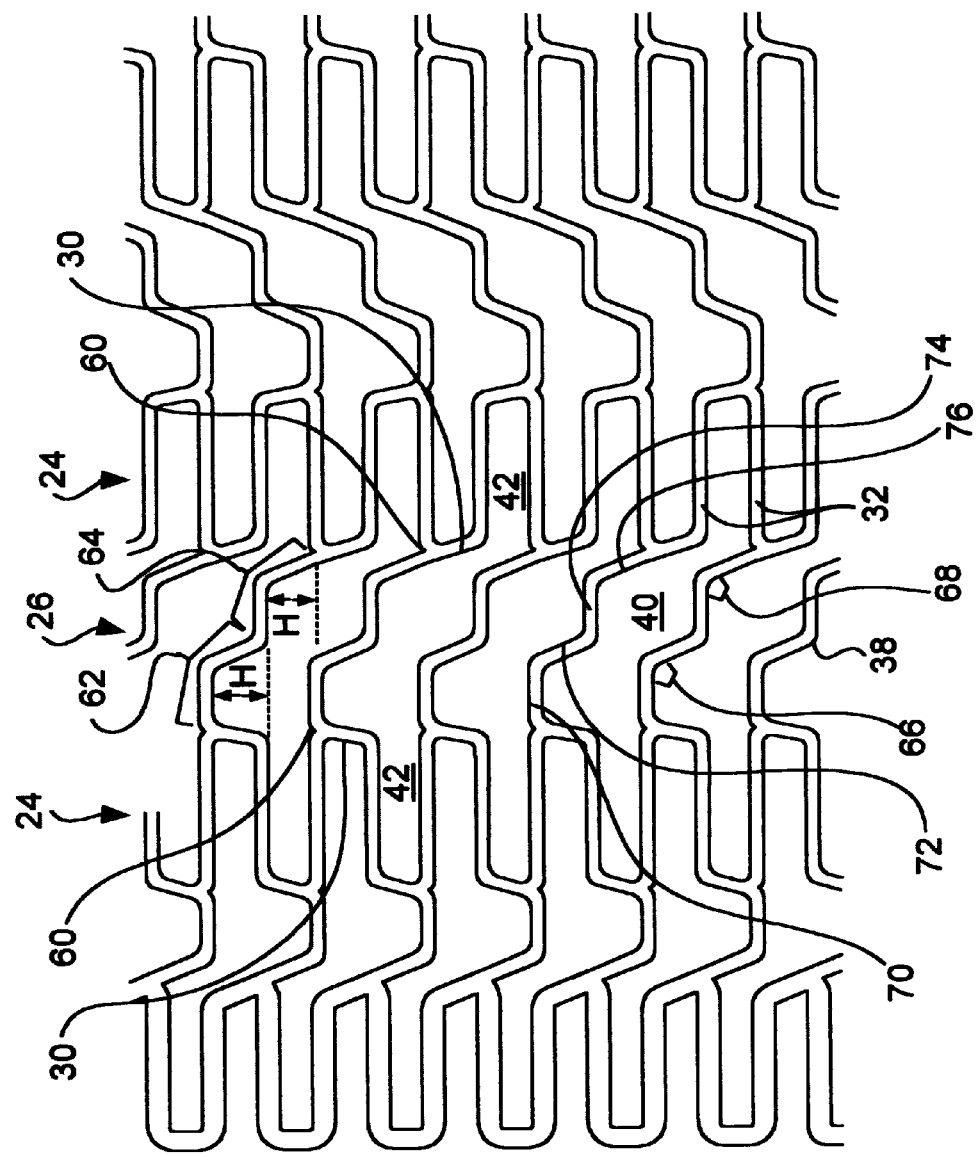
FIG. 3B is a close up view of the strut pattern of FIG. 3A.

Referring now to FIGS. 3A and 3B, connecting struts 38 have a first stair-step 62 and a second stair-step 64. At least a portion of the plurality of geometric cells 40 are asymmetrical geometric cells.

First stair-step 62 defines a first slant angle 66 and second stair-step 64 defines a second slant angle 68. An arc of first slant angle 66 can be the same or different than an arc of second slant angle 68. First stair-step 62 has a first substantially linear section 70 and a second substantially linear section 72. Second stair-step 64 has a first substantially linear section 74 and a second substantially linear section 76. The lengths of substantially linear sections 70 through 76 can be same or different in various combinations. First stair-step and the second stair-step have the same or different heights "H". Additionally, first and second stair-steps 62 and 64 can the same or different lengths. Stress relief notches 60 can be formed in first and second stair-steps 62 and 64. In FIGS. 3A and 3B, connecting struts 38 are coupled at both proximal and distal ends to corners of joining struts 30.

Figure 4A:
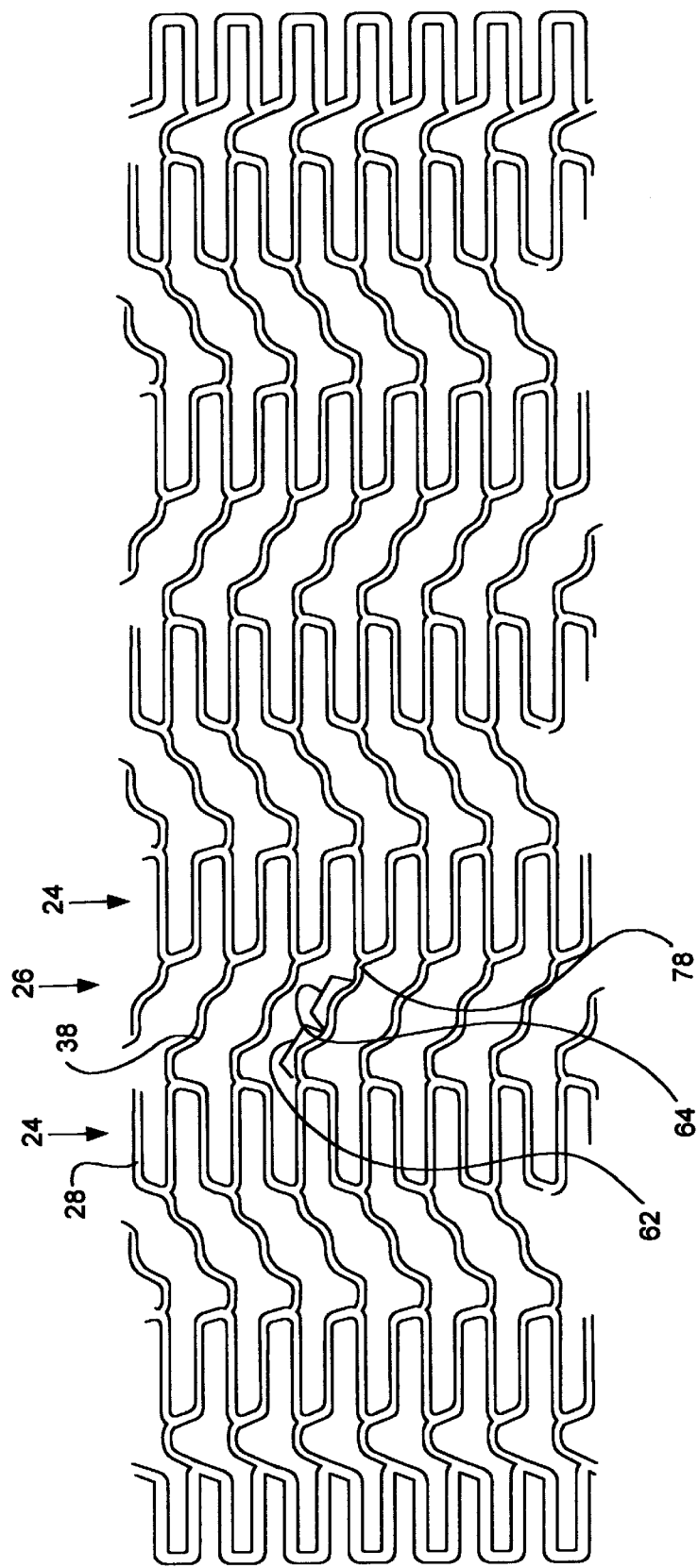
FIG. 4A is a drawing of another embodiment of a strut pattern of the stent of the present invention.
Figure 4B:
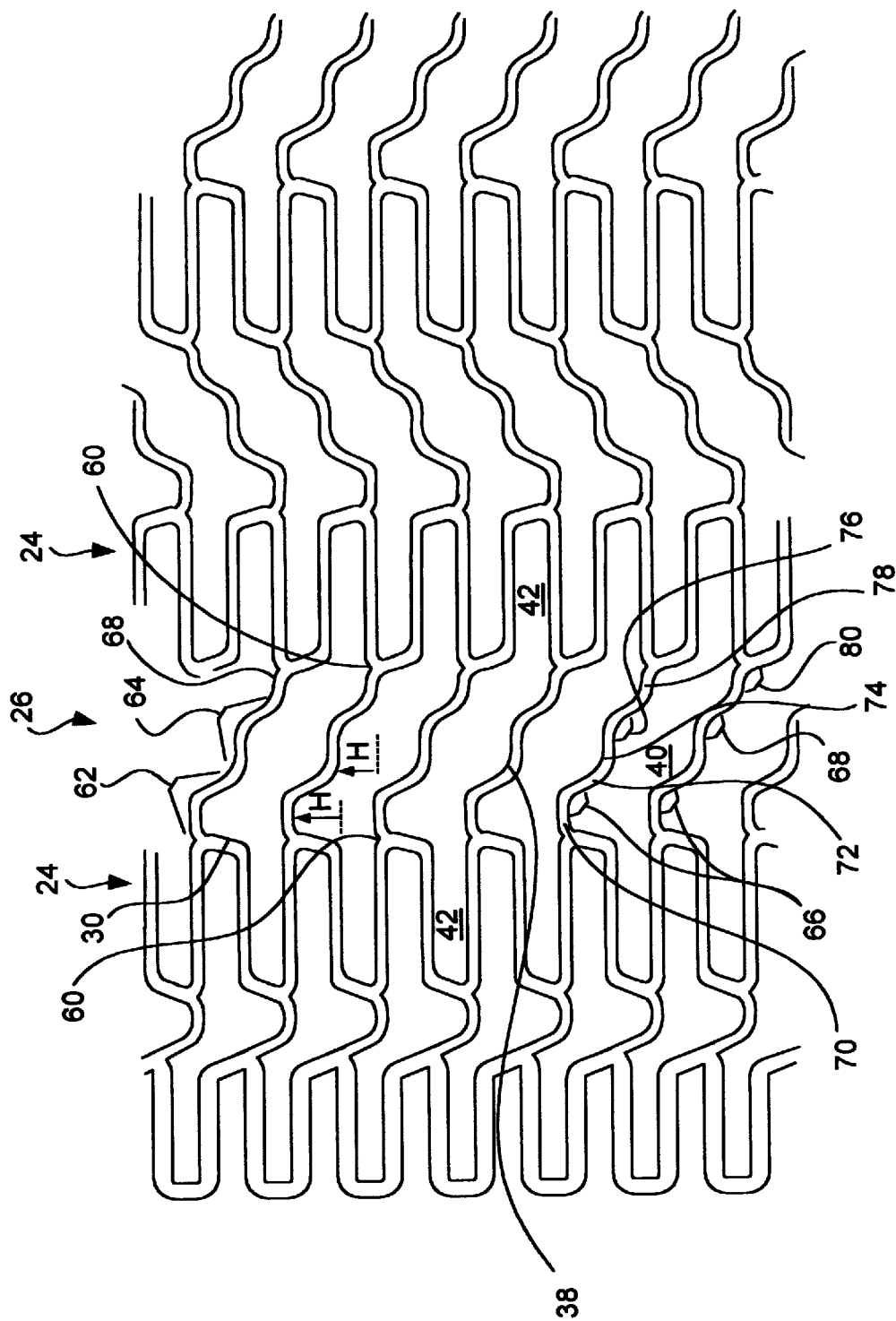
FIG. 4B is a close up view of the strut pattern of FIG. 4A.

In the embodiment of FIGS. 4A and 4B, second stair-step 64 further includes a tail section 78 coupled to joining strut 30. Stress relief notches 60 are formed at the proximal end of first stair-step 62 and at tail section 78. First substantially linear section 70 and tail section 78 are each coupled to corners of joining struts 30.

Figure 5A:
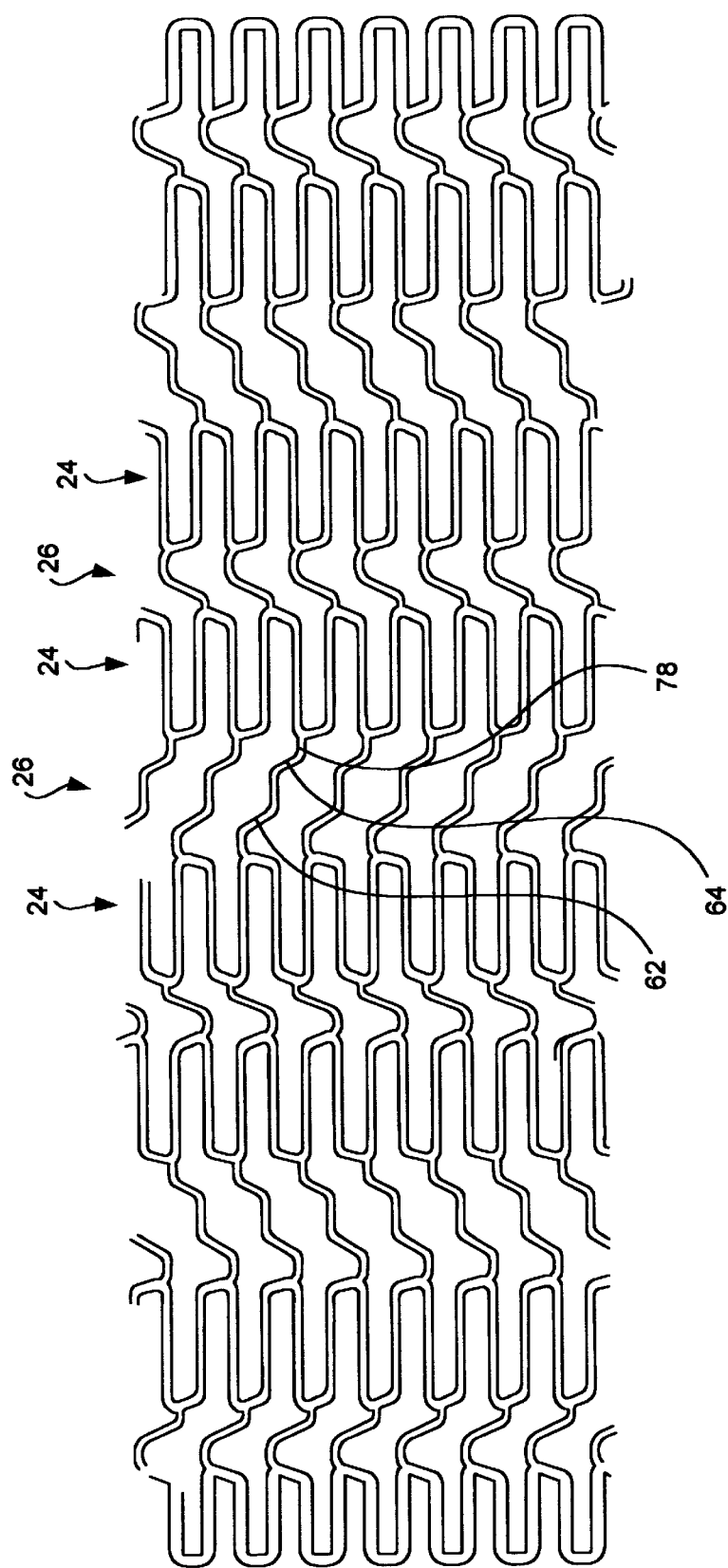
FIG. 5A is a drawing of another embodiment of a strut pattern of the stent of the present invention.
Figure 5B:
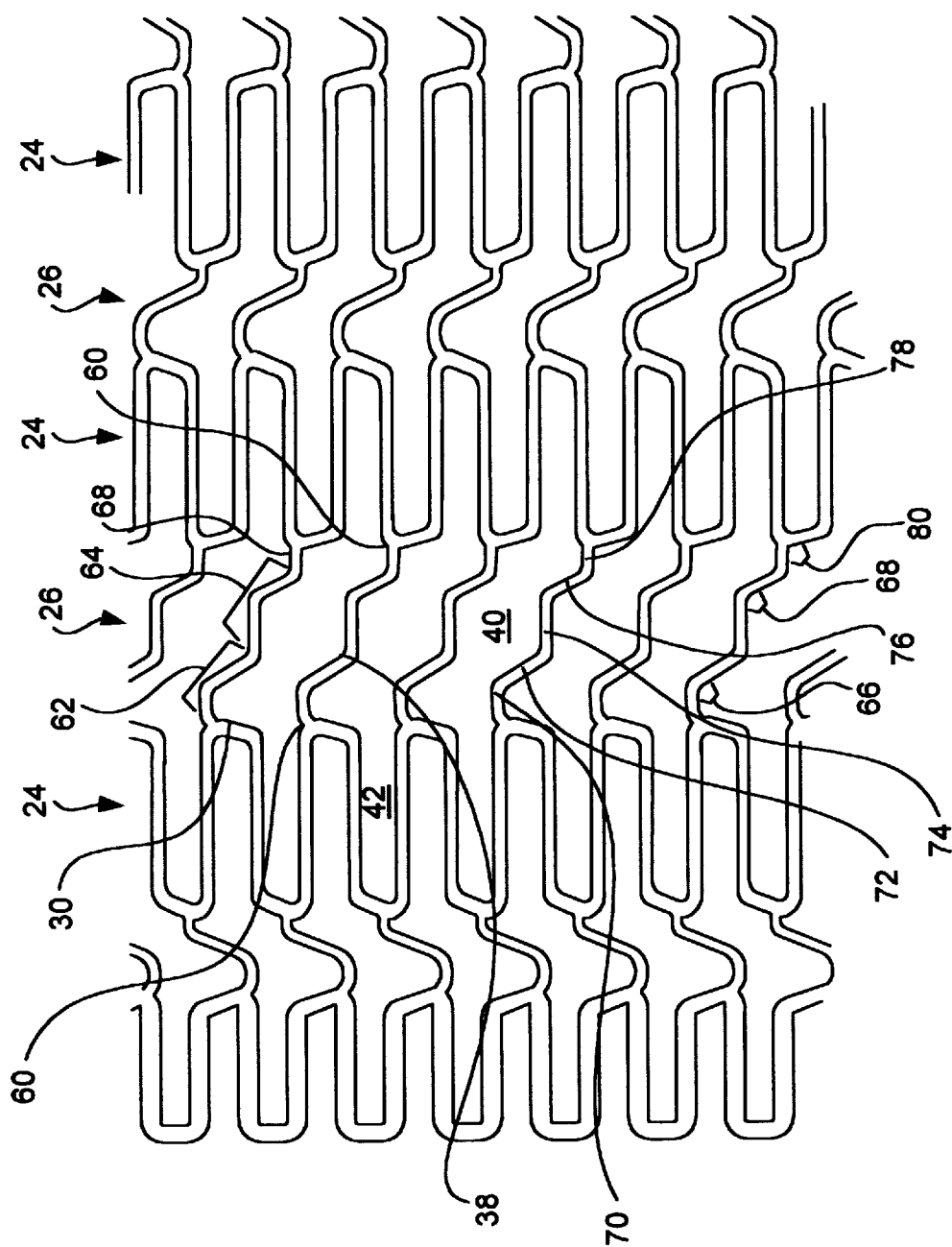
FIG. 5B is a close up view of the strut pattern of FIG. 5A.

In the embodiment of FIGS. 5A and 5B, first linear section 70 is coupled to a corner of joining strut 30, while tail section 78 is coupled to an intermediate section of joining strut 30. Stress relief notches are formed at both couplings. A third slant angle 80 is formed between tail section 78 and joining strut 30.

Figure 6:
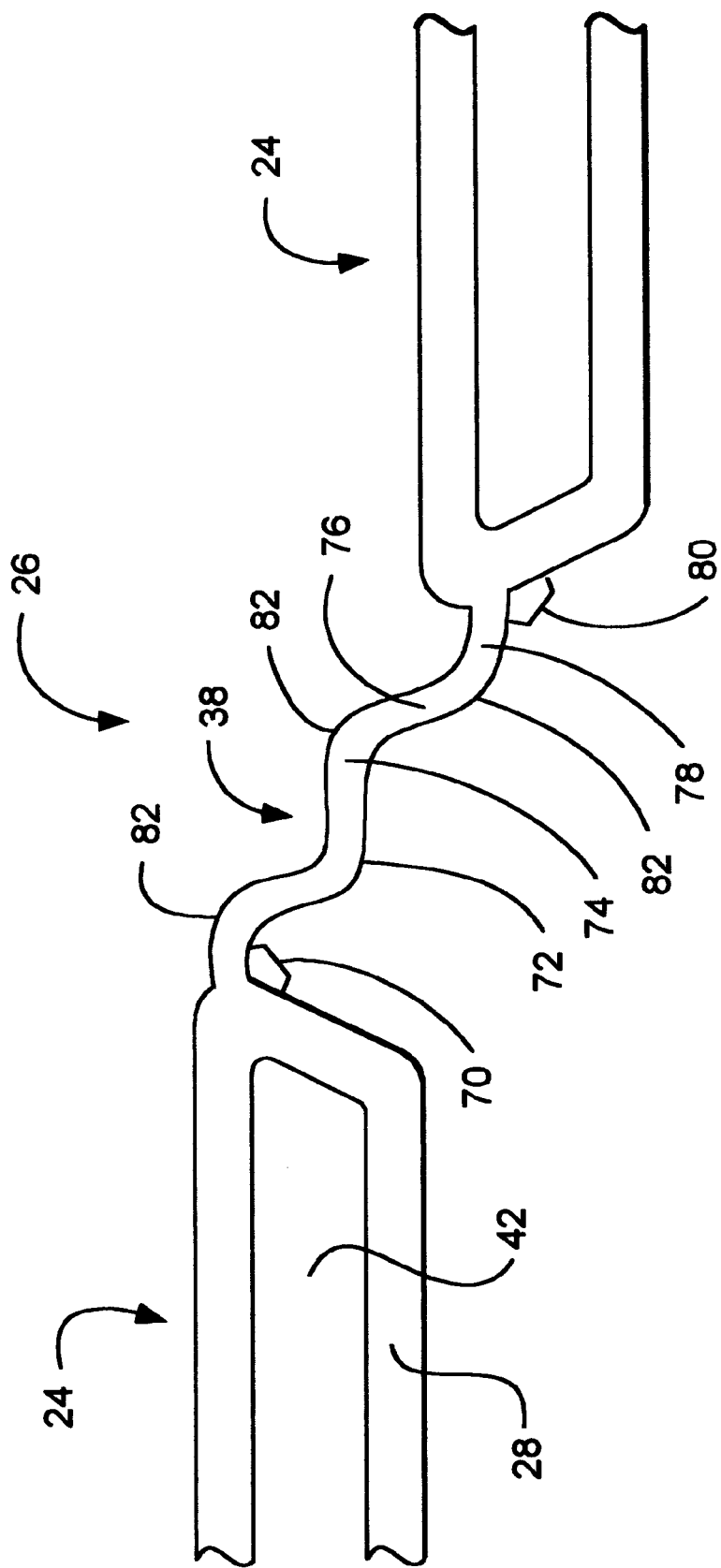
FIG. 6 is a drawing of another embodiment of a strut pattern of the stent of the present invention.

In the embodiment of FIG. 6, first and second stair-steps 62 and 64 each have one or more radii of curvature 84. In the embodiment of FIG. 7, connecting strut 38 includes three vertex 84. The first and third vertex 84 extend in a first direction, while the intermediate vertex 84 extends in an opposite direction. In the embodiment of FIG. 8, there are only two vertex's 84. The two vertex's 84 are coupled by a linear section 86.

In the embodiment of FIG. 9, connecting strut 38 includes one or more trapezoidal wave structures 88. As shown in FIG. 9, first and third trapezoidal wave structures 88 extend in a first direction, while the second trapezoidal wave structure 88 extends in an opposite direction. First and second trapezoidal wave structures 88 are coupled to a corner of joining strut 30. In FIG. 10, the first and third trapezoidal wave structures 88 each include a tail section 90 that is coupled to an intermediate section of a joining strut 30.

Figure 11:
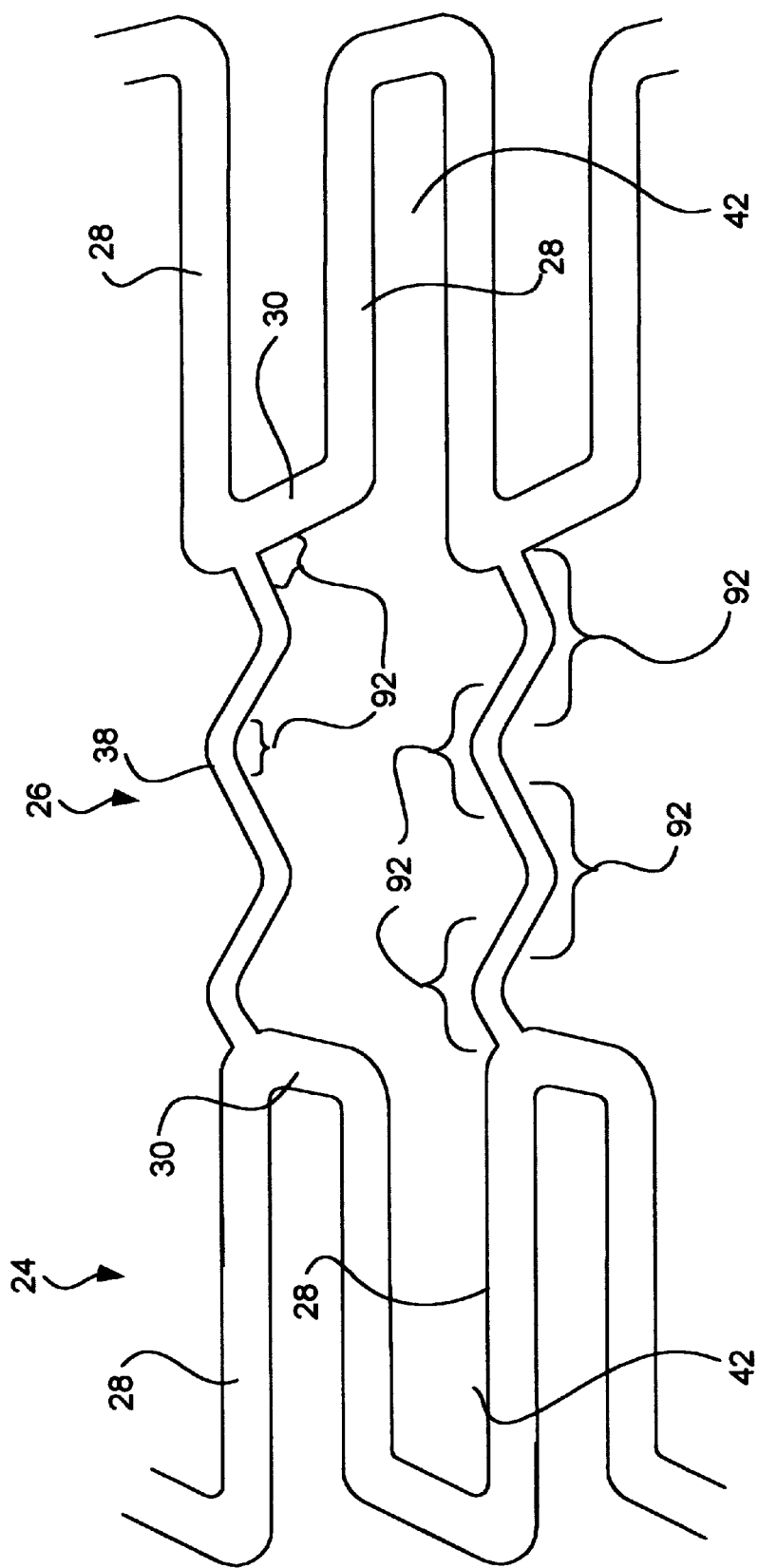
FIG. 11 is a drawing of another embodiment of a strut pattern of the stent of the present invention.
Figure 12:
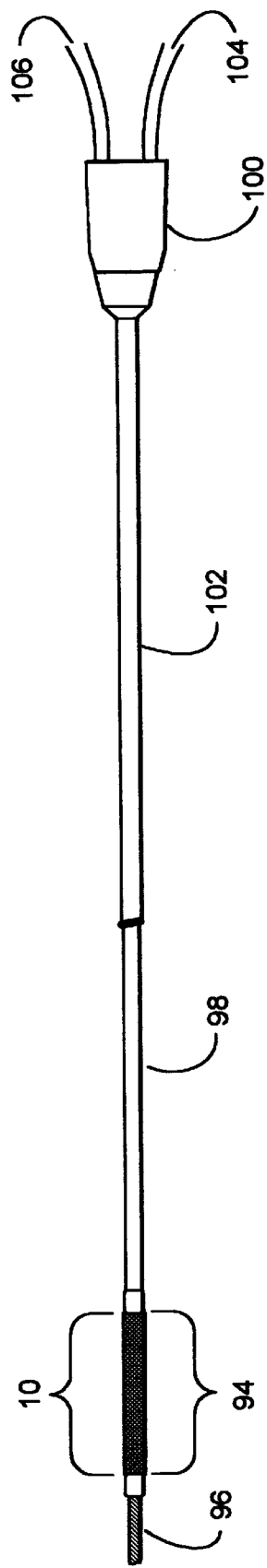
FIG. 12 is drawing of a delivery balloon catheter, illustrating a method of deliver of a stent in accordance with the present invention.

In the embodiment of FIG. 11, connecting strut 38 includes one or more elbow sections 92. In FIG. 11, the proximal and distal elbow sections 92 are coupled to corners of joining strut 30. It will be appreciated that one or both of the proximal or distal elbow sections 92 may be coupled to an intermediate section of a joining strut 30.

Stent 10 of the present invention can be made using a CAM-driven laser cutting system to cut stent 10 pattern from a stainless steel tube. The rough-cut stent is preferably elector-polished to remove surface imperfections and sharp edges. Other methods of fabricating stent 10 can also be used such as EDM, photo-electric etching technology, or other methods. Any suitable material can be used for stent 10 including other metals and polymers so long as they provide the essential structural strength, flexibility, biocompatibility and expandability.

Stent 10 is typically at least partially plated with a radiopaque metal, such as gold, platinum, tantalum or other suitable metal. It is preferred to plate only both ends of stent 10 by localized plating; however, the entire stent or other regions can also be plated. When plating both ends, one to three or more expansion columns on each end of stent 10 are plated to mark the ends of stent 10 so they can be identified under fluoroscopy during the stenting procedure. By plating stent 10 only at the ends, interference of the radiopaque plating material with performance characteristics or surface modulation of the stent frame is minimized. Additionally the amount of plating material required is reduced, lowering the material cost of stent 10.

After plating, stent 10 is cleaned, typically with detergent, saline and ultrasonic means that are well-known in the art. Stents 10 are then inspected for quality control, assembled with the delivery balloon catheter, and properly packaged, labeled, and sterilized.

Stent 10 can be marketed as stand alone or as a premounted delivery balloon catheter assembly. Referring to FIG. 9, stent 10 is crimped over a folded balloon 94 at the distal end 96 of a delivery balloon catheter assembly 96. The assembly 96 includes a proximal end adapter 98, a catheter shaft 100, a balloon channel 102, a guidewire channel 104, a balloon 94, and a guidewire 106. Balloon 94 can be tapered in an expanded state, be curved from a proximal end to a distal end in the expanded state. Additionally stent 10 can be non-tapered or tapered in the expanded state.

Typically the guidewire 106 is inserted into the vein or artery and advanced to the target site. The catheter shaft 100 is then forwarded over the guidewire 106 to position stent 10 and balloon 94 into position at the target site. Once in position balloon 94 is inflated through balloon channel 102 to expand stent 10 from a crimped to an expanded state. In the expanded state, stent 10 provides the desired scaffolding support to the vessel. Once stent 10 has been expanded, balloon 94 is deflated and catheter shaft 100, balloon 94, and guidewire 106 are withdrawn from the patient.

Stent 10 can be made as short as less than 10 mm in length or as long as 100 mm or more. If long stents are to be used, however, matching length delivery catheter balloons will typically be needed to expand stents 10 into their deployed positions. Long stents, depending on the target vessel, may require curved long balloons for deployment. Curved balloons which match the natural curve of a blood vessel reduce stress on the blood vessel during stent deployment. This is especially important in many coronary applications which involve stenting in curved coronary vessels. The use of such curved balloons is within the scope of the present invention.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A stent in a non-expanded state, comprising:
   a first column expansion strut pair, a plurality of the first column expansion strut pair forming a first expansion column;
   a second column expansion strut pair, a plurality of the second column expansion strut pair forming a second expansion column; and
   a first serial connecting strut, a plurality of first serial connecting struts forming a first connecting strut column, the plurality of first serial connecting struts coupling the first expansion column to the second expansion column and at least a portion of the plurality of the first serial connecting struts have a first stair-step with a first slant angle arc of greater than 90° and a second stair-step stair-step with a second slant angle arc of greater than 90°; and
   wherein the first expansion column, the second expansion column, and the first connecting strut column form a plurality of geometric cells and at least a portion of the plurality are asymmetrical geometric cells.

2. The stent of claim 1, wherein the first column expansion strut pair defines a first column loop slot, and the second column expansion strut pair defines a second column loop slot.

3. The stent of claim 1, wherein the first stair-step and the second stair-step of the first serial connecting strut each have a different length.

4. A stent in a non-expanded state, comprising:
   a first expansion column formed of a plurality of first expansion struts;
   a second expansion column formed of a plurality of second expansion struts;
   a first connecting strut column formed of a plurality of first connecting struts, wherein the first connecting strut column couples the first expansion column to the second expansion column and at least a portion of the plurality of first connecting struts include a first stair-step with a first slant angle arc of greater than 90° and a second stair-step with a second slant angle arc of greater than 90°.

5. The stent of claim 4, wherein an arc of the first slant angle is different from an arc of the second slant angle.

6. A stent in a non-expanded state, comprising:
   a first expansion column formed of a plurality of first expansion column strut pairs, a first expansion column first strut pair including a first expansion strut adjacent to a second expansion strut and a first expansion column first joining strut that couples the first and second expansion struts at a distal end of the first expansion strut pair, the first expansion column first joining strut having a first joining strut first corner and a first joining strut second corner;
   a second expansion column formed of a plurality of second expansion column strut pairs, a second column first expansion strut pair including a first expansion strut adjacent to a second expansion strut and a second expansion column first joining strut that couples the first and second expansion struts at a proximal end of the first expansion strut pair, the second expansion column first joining strut having a first joining strut first corner and a first joining strut second corner; and
   a first serial connecting strut coupling the first expansion column first joining strut to the second expansion column first joining strut, the first serial connecting strut including a first stair-step stair-step with a first slant angle arc of greater than 90° and a second stair-step with a second slant angle arc of greater than 90°.

7. The stent of claim 6, wherein the first stair-step is coupled to the first joining strut first corner of the first expansion column first joining strut, and the second stair-step is coupled to the first joining strut first corner of the second expansion column first joining strut.

8. The stent of claim 6, wherein a stress relief notch is formed in the first stair-step.

9. The stent of claim 7, wherein the first stair-step includes a stress relief notch formed where the first stair-step is coupled to the first joining strut first corner of the first expansion column first joining strut.

* * * * *